(12) United States Patent
Ashley et al.

(10) Patent No.: US 6,850,013 B1
(45) Date of Patent: Feb. 1, 2005

(54) INFRARED LIGHT EMITTING DIODES

(75) Inventors: Timothy Ashley, Malvern (GB); John Graham Crowder, Edinburgh (GB); Stanley D. Smith, Edinburgh (GB); Volker P Manheim, Jever (DE)

(73) Assignee: QinetiQ Limited, London (GB)

( * ) Notice: Subject to any disclaimer, the term of this patent is extended or adjusted under 35 U.S.C. 154(b) by 0 days.

(21) Appl. No.: 09/743,039

(22) PCT Filed: Jul. 2, 1999

(86) PCT No.: PCT/GB99/02117

§ 371 (c)(1),
(2), (4) Date: Jul. 25, 2001

(87) PCT Pub. No.: WO00/02263

PCT Pub. Date: Jan. 13, 2000

(30) Foreign Application Priority Data

Jul. 4, 1998 (GB) ............................................. 9814462

(51) Int. Cl.[7] ................................................ G09G 3/10
(52) U.S. Cl. ............................ 315/169.1; 257/E31.099; 257/E31.113
(58) Field of Search .......................... 315/169.1, 169.3, 315/150; 257/184, E31.054, E31.108, E31.099, E31.113; 372/12, 29.012, 29.014, 30

(56) References Cited

U.S. PATENT DOCUMENTS

| 5,016,073 A | * | 5/1991 | Elliott et al. ................. 257/184 |
| 5,214,292 A | * | 5/1993 | Hendrick, Jr. ............. 250/495.1 |
| 5,251,225 A | * | 10/1993 | Eglash et al. .................. 372/45 |
| 5,625,635 A | * | 4/1997 | Kurtz et al. ................... 372/45 |

FOREIGN PATENT DOCUMENTS

EP WO97/13282 * 4/1997

OTHER PUBLICATIONS

Phillips C et al.: "Recent advances in In(As, Sb) SLS and QW LEDs for the 3–10 micron region" Light Emitting Diodes: Research, Manufacturing, and Applications II, San Jose, CA, USA, Jan. 28–29, 1998, vol. 3279, pp. 154–160, Proceedings of the SPIE–The International Society for Optical Engineering, 1998, Spie–Int. Soc. Opt. Eng, USA.

Elliott C T: "New Infrared and other applications of narrow–gap semiconductors" Infrared Technology and Applications XXIV, San Diego, CA, USA, Jul. 19–24, 1998, vol. 3436, pt. 1–2, pp. 763–775, Proceedings of the SPIE–The International Society for Optical Engineering, 1998, SPIE–Int. Soc. Opt. Eng, USA.

Ashley T: "Electronic and Optoelectronic Devices in Narrow–Gap Semiconductors" Institute of Physics Conference Series, No. 144, Jan. 1995, pp. 345–352.

Wang C H et al.: "Detection of Nitrogen Dioxide Using a Room Temperature Operation Mid–Infrared INSB Light Emitting Diode" Electronics Letters, vol. 34, No. 3, Feb. 1998, pp. 300/301.

* cited by examiner

Primary Examiner—Haissa Philogene
(74) Attorney, Agent, or Firm—Nixon & Vanderhye P.C.

(57) ABSTRACT

An infrared light emitting diode arrangement comprising an infrared light emitting diode which emits positive luminescence when forward biased and emits negative luminescence when reverse biased. The diode is driven by an alternating forward and reverse bias input so that the difference in output power between the positive luminescence and the negative luminescence of the light emitting diode is stabilised with respect to temperature. The infrared light emitting diode arrangement has particular application as a source in gas sensors and reduces or eliminates temperature control requirements for infrared light emitting diode sources.

16 Claims, 6 Drawing Sheets

INFRARED LIGHT EMITTING DIODES

This application is the U.S. national phase of International Application No. PCT/GB99/02117, filed 2 Jul. 1999, which designated the U.S., the entire content of which is hereby incorporated by reference.

FIELD OF THE INVENTION

This invention relates to semiconductor light emitting diodes (LEDs), which emit electromagnetic radiation at infrared wavelengths. Infrared LEDs have applications in the fields of telecommunications, spectroscopy and, in particular, gas sensors.

BACKGROUND OF THE INVENTION

Infrared gas sensor technology is well established and can give selective and quantitative gas detection for a variety of gasses having vibrational-rotational absorptions at wavelengths of between 3 and 12 microns. Existing infrared sources for gas sensors at infrared wavelengths operate at high temperatures and thereby have a number of drawbacks in intrinsic safety, wavelength range, stability and life. Furthermore, existing sources emit pulses of infrared radiation at a frequency which is limited by a maximum frequency of the order of several Hertz which is not consistent with optimum working frequencies of processing electronics and limits the type of infrared signal detector which can be used in the gas sensor.

Recently developed infrared LEDs overcome the bulk of these problems in gas sensor applications. The new infrared light emitting diodes are intermittently positively biased in order to generate a series of pulses of infrared radiation. However, the output power of these pulses is strongly dependent on temperature. Accordingly, during use of such an infrared LED in gas sensor arrangements, either the LED temperature has to be monitored and the results mathematically corrected for temperature changes or the LED temperature has to be stabilised. The normal method for stabilising optical output power with respect to temperature is the use of temperature control methods, such as the combination of thermoelectric or Peltier cooling and temperature sensors. Therefore, stabilising and/or monitoring temperature adds expense and complexity to the operation of infrared LEDs in gas detection applications.

A dynamic infrared scene projector comprising infrared light emitting diodes capable of emitting both positive and negative luminescence is discussed in International Patent Application Number PCT/GB96/02374. A gas sensor including an infrared light emitting diode which can emit both positive and negative luminescence is described in an article by C. H. Wang et al entitled "Detection of nitrogen dioxide using a room temperature operation mid-infrared InSb light emitting diode" which was published in Electronics Letters, vol. 34, No. 3 (5 Feb. 1998), pages 300–301.

SUMMARY OF THE INVENTION

The object of the present invention is to provide an infrared LED arrangement which does not require significant temperature stabilisation in order to operate in a stable manner.

Accordingly, a first aspect of the present invention provides an infrared light emitting diode arrangement comprising;

an infrared light emitting diode which emits positive luminescence when forward biased and negative luminescence when reverse biased, and a drive means for supplying an alternating forward and reverse bias input to the light emitting diode;

characterised in that the levels of forward and revere bias applied by the drive means are set so that at the forward bias input level the change in output power of the LED with temperature is substantially equal to and cancels out the change in the output power of the LED with temperature at the reverse bias input level over a selected temperature range so that the difference in output power between the positive luminescence and the negative luminescence of the light emitting diode is stabilised with respect to temperature.

According to a second aspect of the present invention there is provided a method of operating an infrared light emitting diode which emits positive luminescence in forward bias and negative luminescence in reverse bias, the method comprising supplying an alternating forward and reverse bias input to the light emitting diode characterised in that the levels of forward and reverse bias are selected so that the change in output power of the LED with temperature is substantially equal to and cancels out the change in the output power of the LED with temperature at the reverse bias input level over a selected temperature range so that the difference in output power between the positive luminescence and the negative luminescence of the light emitting diode is stabilised with respect to temperature.

The component of the output power emitted from the light emitting diode (LED) which varies with the alternating forward and reverse bias input therefore has a constant difference between the maximum (positive luminescence) and the minimum (negative luminescence) output power in each cycle of positive and negative luminescence, over a selected range of temperatures. Accordingly, if the minimum negative luminescence is used as a base level for measurements of output power, then the difference between this base level (which will change with temperature) and the maximum level of positive luminescence (which will also change with temperature) will remain constant over a selected range of temperatures for each cycle of positive and negative luminescence. The thus temperature stabilised alternating output power can be used as the source in various infrared applications, in particular in gas sensors, with little or no external temperature control.

The infrared diode arrangement according to the present invention can also increase the amplitude of the usable infrared signal, because the negative luminescence pulse can be used as well as the positive luminescence pulse, for example, in gas sensor applications.

Figure 4A:
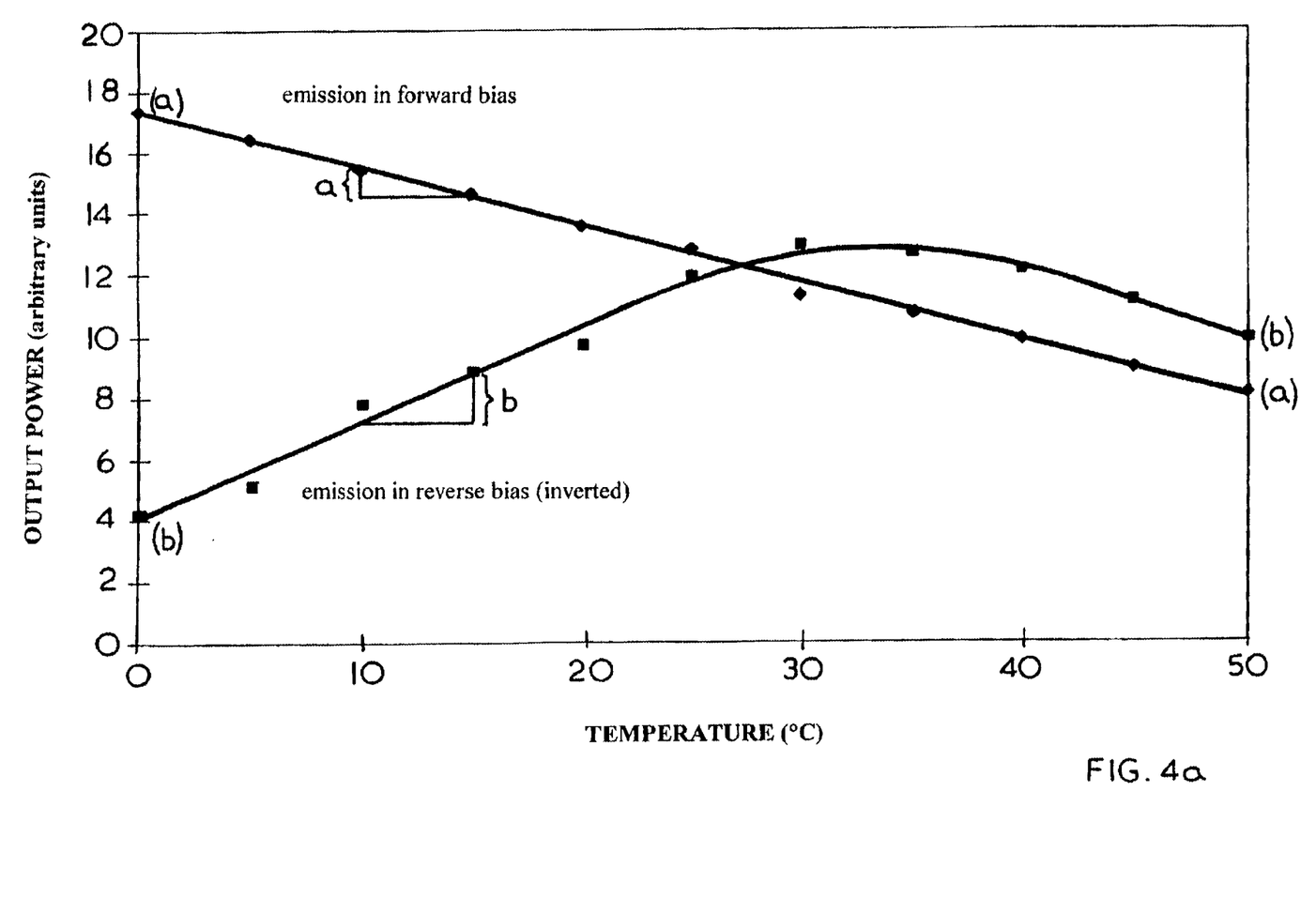
FIG. 4a is a graph showing the temperature dependence of the positive luminescence of the output power of the type of LED shown in FIG. 1 in forwards bias and the negative luminescence of the type of LED shown in FIG. 1 in reverse bias.
Figure 4B:
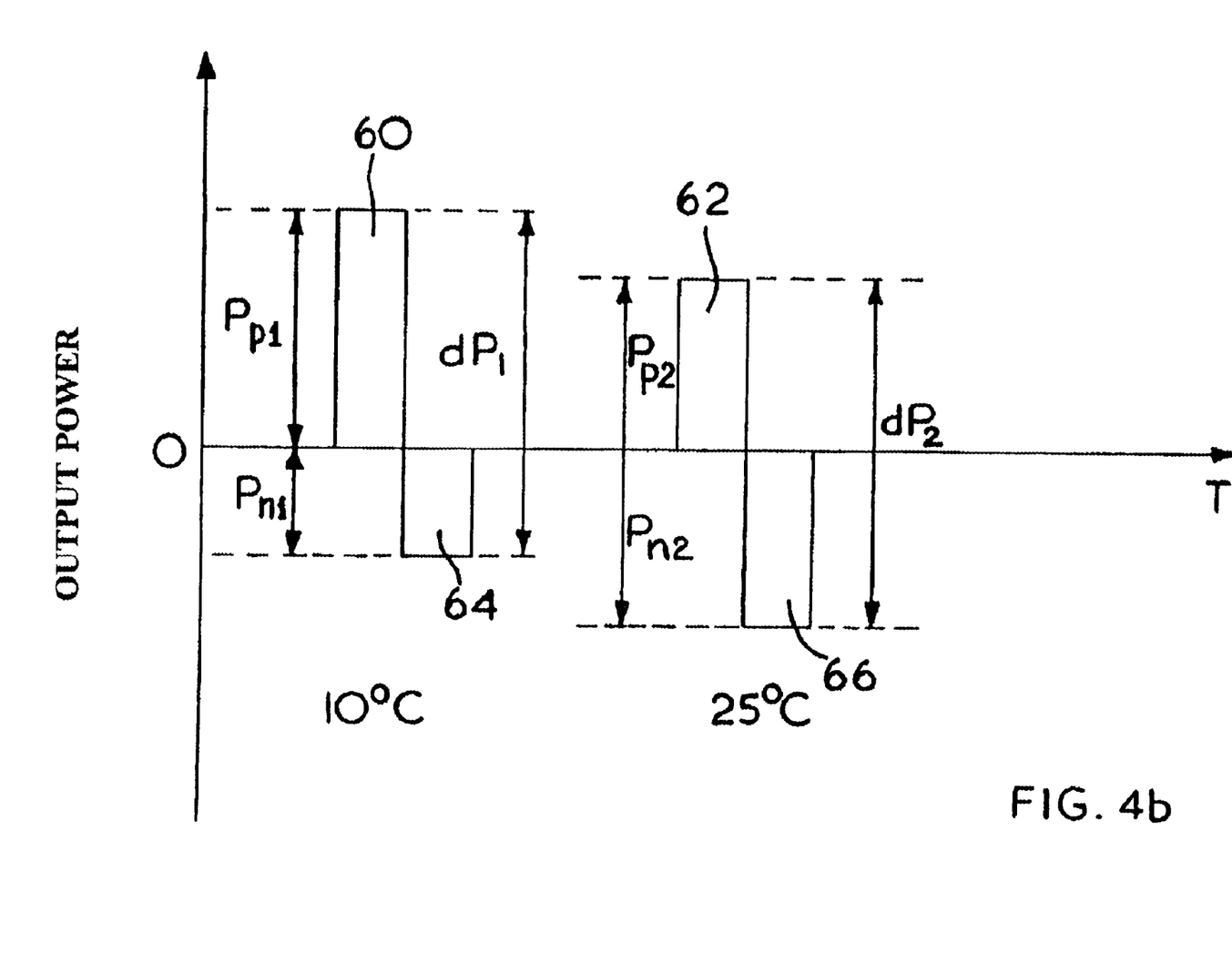
FIG. 4b shows single cycles of positive and negative luminescence for the type of LED shown in FIG. 1 at temperatures of 10° C. and 25° C.

This can be understood with reference to FIG. 4a which shows the variation of positive luminescence and negative luminescence (inverted) with temperature for a sample infrared LED and FIG. 4b which shows a single positive and negative luminescence cycle for a sample infrared LED at two difference temperatures. It can be seen in FIG. 4a that positive luminescence (emission in forward bias), for the semiconductor infrared LED measured in FIG. 4a decreases steadily with an increase in temperature in the range of at least 0 to 50° C. This is as a consequence of the ratio of the temperature dependencies of the radiative and dominant non-radiative recombination mechanisms within the LED. This is also shown in FIG. 4b, in which at 10° C. the output power in positive luminescence is $P_{P1}$ and at 25° C. the output power in positive luminescence is reduced to $P_{P2}$. For negative luminescence (emission in reverse bias), it can be seen from FIG. 4a, that there is a steady increase in intensity with temperature from below 0° C. to approximately 35° C. This is a consequence of the LED being under reverse saturation over this temperature range so that the negative luminescence intensity is primarily related to radiative processes within the LED This is also shown in FIG. 4b, in which at 10° C. the output power in negative luminescence is $P_{N1}$ and at 25° C. the output power in negative luminescence has a greater intensity (ie. is more negative) at $P_{N2}$. However, by selecting the correct bias level for forward and reverse bias, over selected temperature ranges, the change in positive luminescence from 10° C. to 25° C. can be made substantially the same as and cancelled out by the change in negative luminescence. This gives rise to a constant difference between output power of the positive luminescence and the negative luminescence for each cycle. This is shown in FIG. 4b, because $dP_1=dP_2$.

Therefore, it is preferred that the level of forward and reverse bias are chosen so that in forward bias the change in output power of the LED with temperature is substantially equal to and cancels out the change in output power of the LED with temperature in reverse bias, over a selected temperature range.

By operating the LED measured in FIG. 4a with an alternate forward and reverse bias input so that the LED operates with alternate positive and negative luminescence the temperature dependencies shown in FIG. 4a can be made to cancel each other out in selected temperature ranges between 0° C. and 35° C. Thus the sensitivity to temperature of the difference in output power between positive luminescence and negative luminescence is reduced. The temperature ranges over which reduced sensitivity to temperature is achieved correspond to the practical operating temperatures of infrared LEDs. This enables the LED arrangement according to the present invention to be operated with much simplified temperature stabilisation techniques.

In order to improve temperature stabilisation, the alternating forward and reverse bias input alternates regularly. In particular it is preferred that the period and/or intensity of forward bias input is substantially the same in consecutive cycles of positive luminescence and the period and/or intensity of reverse bias input is substantially the same in consecutive cycles of negative luminescence. However, the period and/or intensity of forward bias input does not have to be the same as the respective period and/or intensity of the reverse bias input.

In order to achieve maximum output power, while still achieving temperature stabilisation, the reverse bias level is chosen so that it gives the maximum negative luminescence, at the maximum temperature in a selected temperature range of operation. Then the forward bias level is chosen as described above. The positive and negative luminescence of the LEDs described herein increase with applied bias levels, for example, with increased bias current, until saturation occurs in reverse bias. Therefore, in order to achieve the maximum output powers while still achieving temperature stabilisation it is preferred that the reverse bias level is chosen to be the minimum necessary to give a current close to the saturation current.

In a preferred embodiment the frequency of the alternating bias input signal is at least 1 Hz and preferably at least 5 Hz. The frequency of the alternating bias input signal must be high enough so that temperature dependent changes in output power during a half cycle of the signal (ie. temperature dependant output power changes during each period of forward bias or reverse bias) are negligible. The upper limit to the frequency is limited only because the response of the infrared LED to the change between forward and reverse bias is not instantaneous. The present invention should be effective up to frequencies of at least several tens of megahertz.

In a preferred embodiment the light emitting diode emits radiation at infrared wavelengths in the range of 3 to 13 microns.

In a further preferred embodiment the light emitting diode is formed from a narrow bandgap semiconductor material.

According to a third aspect of the present invention there is provided a sensor device including an infrared light emitting diode which is temperature stabilised as described above. The fight emitting diode according to the present invention is suitable for use in most types of sensors requiring an infrared source, in particular gas sensors.

The present invention provides a temperature stabilised infrared light emitting diode arrangement comprising; an infrared light emitting diode, and a drive means for supplying an alternating forward and reverse bias input to the light emitting diode.

BRIEF DESCRIPTION OF THE DRAWINGS

The present invention will now be described with reference to the following Figures in which.

DETAILED DESCRIPTION OF THE PREFERRED EMBODIMENT

Figure 3:
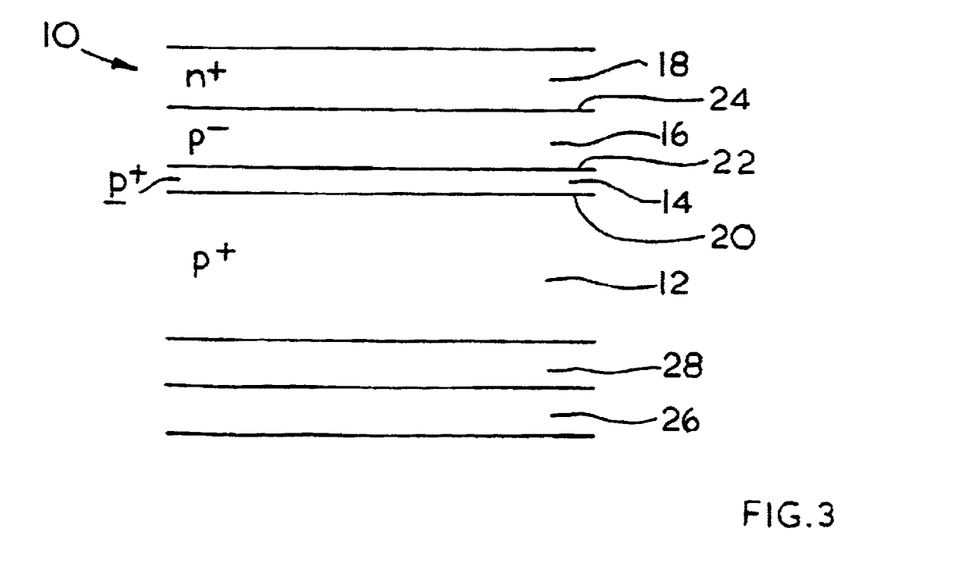
FIG. 3 schematically illustrates a semiconductor hetero structure as grown to produce the device of FIG. 1.

Referring firstly to FIG. 3, there is shown schematically a semiconductor heterostructure (10) suitable for constructing an LED according to the present invention. The heterostructure (10) is based on narrow bandgap material Indium Antimonide (InSb) and comprises Indium Antimonide (InSb) and Indium Aluminium Antimonide ($In_{1-x}Al_xSb$) alloys. Alternative suitable heterostructures could be based, for example, on narrow bandgap material Mercury Cadmium Telluride or Mercury Zinc Telluride.

There are four regions of semiconductor material; a heavily doped p-type ($p^+$) region (12), a relatively wide bandgap heavily doped p-type ($p^+$) region (14), a lightly doped p-type ($p^-$) region (16) and a heavily doped n-type ($n^+$) region (18). In this specification a superscript minus (−) or plus (+) indicates light or heavy doping respectively and the absence of a superscript indicates an intermediate doping level. The bar (_) subscript indicates material of wide bandgap relative to the bandgap of material denoted without a bar subscript. The structure (10) has $p^+\underline{p}^+$ heterojunction (20), $\underline{p}^+p^-$ heterojunction (22) and $p^-p^+$ homojunction (24).

It should be noted that the lightly doped p-type ($p^-$) region (16) could alternatively comprise a lightly doped n-type ($n^-$) material.

The heterostructure (10) is grown in a MBE system on an InSb substrate (26). Adjacent to the substrate (26) is a buffer and temperature ramp region (28) grown whilst the MBE system is being set up correctly to grow heterostructure (10). The growth temperature is approximately 420° C. and the growth rate is 0.5 microns/hr. Mesa diode fabrication is performed using standard photolithographic techniques, on the heterostructure (10), to define chemically etched structures.

The $p^+$ region (12) has a width of approximately 2 microns, the $p^-$ region (16) has a width of around 1 to 3 microns and the $n^+$ region (18) has a width of approximately 1 micron and all are made from InSb which has a bandgap of 0.17 eV at room temperature. The $\underline{p}^+$ region (14) is made of $In_{0.85}Al_{0.15}Sb$ and has a width of 0.02 microns. $In_{0.85}Al_{0.15}Sb$ has a bandgap at room temperature of 0.43 eV, more than twice the bandgap of InSb. Dopants are Silicon (Si) for n-type and Berylium (Be) for p-type. Doping in regions (12) and (14) is $5\times10^{18}$ atoms/cm$^3$, in region (16) is $1\times10^{15}$ atoms/cm$^3$ and in region (18) is $3\times10^{18}$ atoms/cm$^3$.

Figure 1:
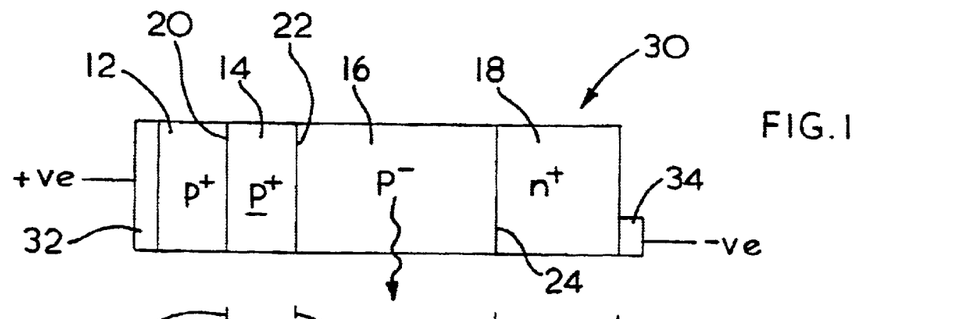
FIG. 1 shows schematically the structure of a semiconductor infrared light emitting diode (LED) suitable for use in the arrangement according to the present invention.

Referring now to FIG. 1, there is shown schematically a semiconductor LED (30). Parts common to FIGS. 1 and 3 are like referenced. As will be described later the $\underline{p}^+p^-$ junction (22) forms an accumulating contact in forward bias and an excluding contact in reverse bias. The $p^-p^+$ junction (24) forms an injecting contact in forward bias and an extracting contact in reverse bias. Electrodes to the diode (30) are provided at (32) and (34) for bias voltage application.

Region (12) provides a narrow bandgap region to which electrode (32) may be attached and the width of this region should be greater than the electron diffusion length, ie. greater than approximately 100 nm. Region (14) must have sufficient width such that minority carriers are substantially prevented from tunnelling between region (16) to region (12), ie. wider than about 10 nm.

Figure 2:
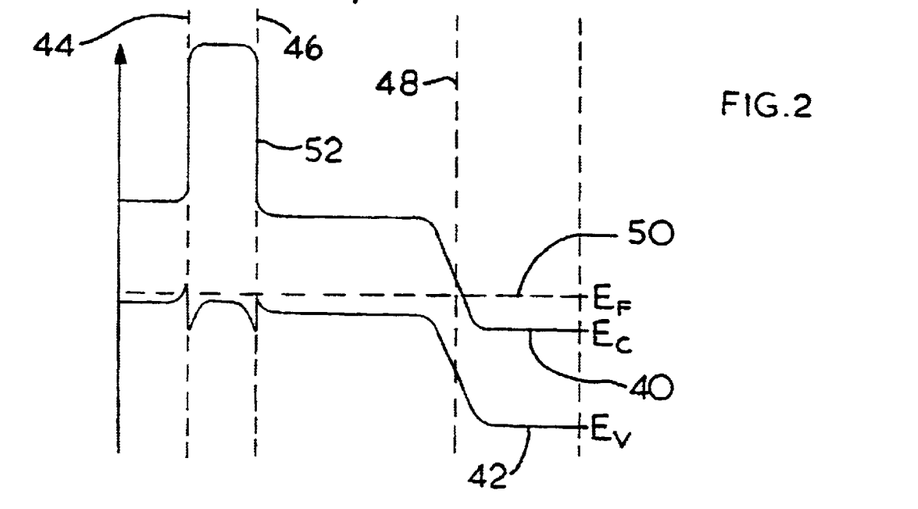
FIG. 2 graphically illustrates the variation in conduction band and valence band edge energies along the LED of FIG. 1.

FIG. 2 shows curves (40) and (42) illustrating graphically the variation in conduction and valance band edge energies $E_c$ and $E_v$ respectively, along the diode (10), at zero bias. Dotted lines (44),(46) and (48) indicate the positions of junctions (20), (22) and (24) respectively. A dashed line (50) indicates the Fermi level $E_F$ through the diode (30). The $\underline{p}^+$ region (14) generates potential barrier (52) in the conduction band $E_c$ which prevents minority carriers (electrons) from the $p^-$ region (16) entering the $\underline{p}^+$ region (12).

The light emitting diode (30) operates as follows. When a forward bias is applied by making contact (32) have a positive voltage with respect to contact (34) majority carriers from each side of the $p^-p^+$ junction (24) cross the junction and enter the material at the other side where they are minority carriers. In this way electrons cross from the $n^+$ region (18) in which they are majority carriers into the $p^-$ region (16) in which they are minority carriers and so cause an increase in the minority carrier population. The excess minority carriers in the $p^-$ region diffuse away from the $p^-p^+$ junction (24) but the build up of minority carriers in the $p^-$ region (16) is very efficient because the minority carriers in the $p^-$ region are accumulated at the $\underline{p}^+$ region (14) by potential barrier (52). The excess minority carriers in the $p^-$ region radiatively recombine with majority carriers and as they do so generate photons of infrared wavelength which are emitted by the diode (30). This causes the positive luminescence of the diode (30).

In reverse bias, when contact (32) has a negative voltage with respect to contact (34), minority carriers from each side of the $p^-n^+$ junction (24) cross the junction and enter the material at the other side where they are majority carriers. In this way electrons from the $p^-$ region (16) in which they are minority carriers cross into the $n^+$ region (18) in which they are majority carriers and so cause a decrease in the minority carrier population of the $p^-$ region (16). This extraction of minority carriers from the $p^-$ region (16) is very efficient because minority carriers from the $\underline{p}^+$ region (12) are prevented from travelling into the $p^-$ region (16) by the potential barrier (52). The reduction of minority carriers in the low doped $p^-$ region has the effect of reducing radiative emission events occurring in the $p^-$ region (16) and causes the relative negative luminescence of the diode (30).

The material and doping for at least the region (18) are chosen so that region (18) is transparent to the photons generated by recombination of electron hole pairs in the $p^-$ region (16). In this way the photons generated in the $p^-$ region (16) can be coupled directly out of the $p^-$ region (16) and indirectly out of the $n^+$ region (18).

FIG. 4a shows at line (a) the variation of the output power emitted with temperature in ° C. for an LED similar to LED (30) of FIG. 1 when forward biased with an 100 mA positive square wave drive current at 1 kHz. The strong dependence of output power on temperature is apparent from FIG. 4a, and it can be seen that the output power reduces approximately linearly with increase in temperature between approximately 0 and 50° C. FIG. 4a also shows at line (b) the variation of the negative luminescence (inverted about the temperature axis) with temperature in ° C. for the same LED when reversed biased with an 100 mA positive square wave drive current at 1 kHz. It can be seen that the inverted negative luminescence increases approximately linearly with increase in temperature between approximately 0 and 35°.

According to the present invention the LED (30) is driven with an alternating polarity bias current, between positive luminescence condition and negative luminescence in order to the achieve the temperature stabilisation of the difference between output power in positive and negative luminescence.

This is shown in FIG. 4b, in which at 10° C. the output power in positive luminescence is $P_{P1}$ and at 25° C. the output power in positive luminescence is reduced to $P_{P2}$. Comparing this to FIG. 4b, in which at 10° C. the output power in negative luminescence $P_{N1}$ and at 25° C. the output power in negative luminescence has a greater intensity (ie. is more negative) at $P_{N2}$. It can be seen that by selecting the correct bias current for forward and reverse bias, over selected temperature ranges, the change in positive luminescence from 10° C. to 25° C. is substantially the same as and cancelled out by the change in negative luminescence. This gives rise to a constant difference between the positive luminescence and the negative luminescence in each cycle as is shown in FIG. 4b, because $dP_1 = dP_2$.

Figure 5:
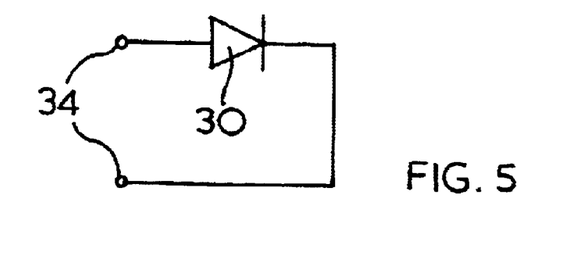
FIG. 5 schematically shows the drive circuit for the LED of FIG. 1.
Figure 6:
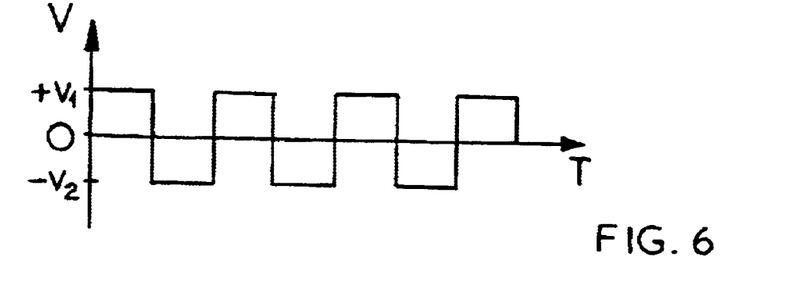
FIG. 6 shows a square wave voltage drive signal which can be input into the drive circuit of FIG. 5.

Referring now to FIG. 5, which shows the light emitting diode (30) in a simple drive circuit. The signal input across input terminals (34) is shown in FIG. 6 and comprises an alternating positive and negative square wave signal with a voltage V which varies between $+v_1$ and $-v_2$ with time t at a frequency of 10 Hz. When the voltage across the diode (30) is $+v_1$, the diode is forwardly biased and so emits a pulse of infrared positive luminescence (for example, as shown in FIG. 4b at (60,62)). When the voltage across the diode (30) is $-v_2$, the diode is reverse biased and emits a pulse of negative luminescence (for example, as shown in FIG. 4b at (64,66)). By alternating between $+v_1$ and $-v_2$ the temperature dependence of the difference in output power between a pulse of positive luminescence and a consecutive pulse of negative luminescence of the LED (30) is substantially reduced (for example, in FIG. 4b $dP_1$ at 10° C. is equal to $dP_2$ at 25° C.) over certain temperature ranges, in particular, within the temperature range of 0° C. to 35° C.

Figure 8A:
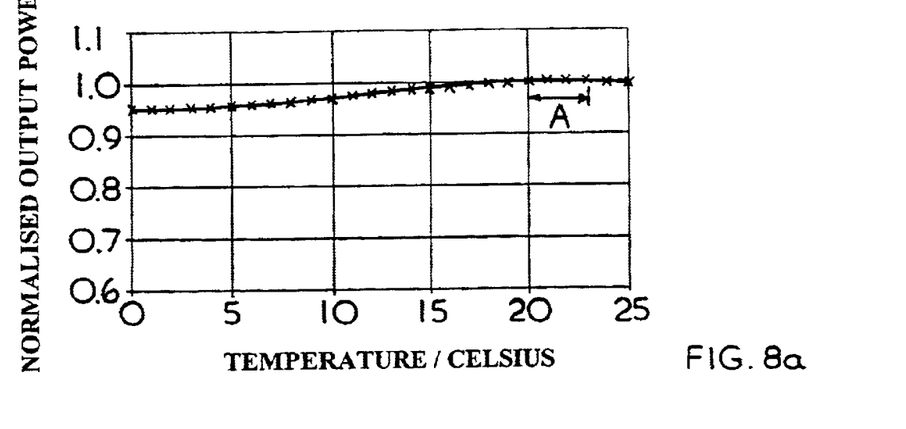
FIGS. 8a to 8c show the temperature dependence of the difference in output power between positive and negative luminescence of the LED arrangement according to the present invention.
Figure 8B:
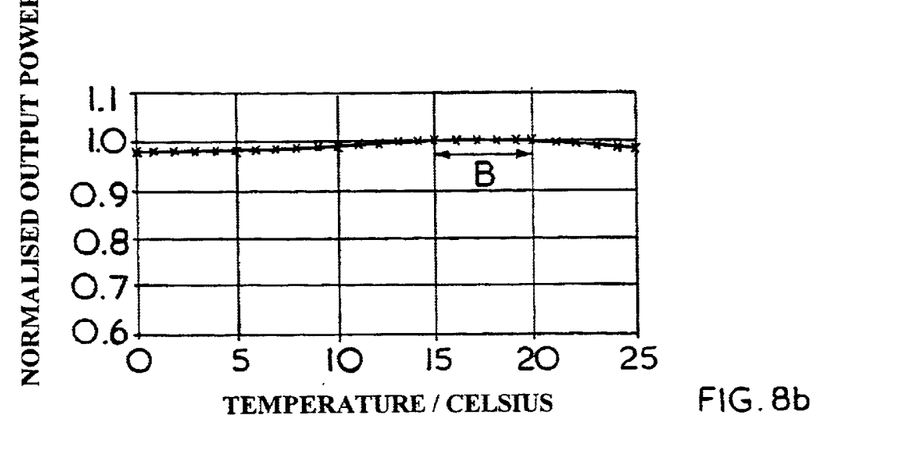
Figure 8C:
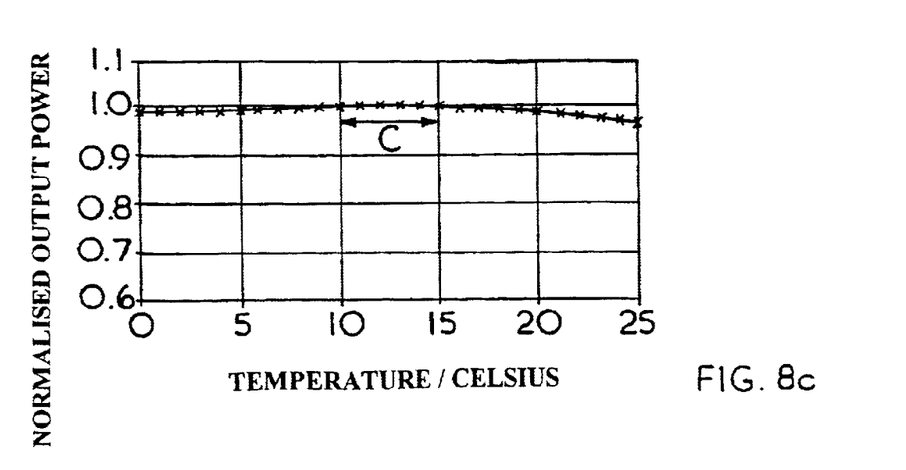

FIGS. 8a to 8c show graphs of the difference in total output power between consecutive pulses of positive and negative luminescence against temperature for a LED of the type described above when it is driven by a positive and negative alternating square wave voltage signal of frequency 10 kHz as described above. In FIG. 8a the forward bias current is 100 mA and the reverse bias current is 70 mA. As can be seen from FIG. 8a the difference in output power is substantially constant over a temperature range A of approximately 3° C., at approximately 20 to 23° C. In FIG. 8b the forward bias current applied to the LED is 100 mA and the reverse bias current is 60 mA. As can be seen from FIG. 8b the difference in output power is substantially constant over a temperature range B of approximately 5° C., at approximately 15 to 20° C. Finally, in FIG. 8c the forward bias current applied to the LED is 100 mA and the reverse bias current is 50 mA. As can be seen from FIG. 8c the difference in output power is substantially constant over a temperature range C of approximately 5° C., at approximately 10 to 15° C.

So far it has been found that using different ratios of forward and reverse bias current, the diode (30) can be operated so that over a temperature range of up to 6° C. the difference in power of the infrared signal output from the diode changes by less than 0.2%. The diode (30) can also be operated with a forward bias current of 100 mA and a reverse bias current of 50 mA so that over a temperature range of up to 14° C. the difference in power of the infrared signal output from the diode changes by less than 1% (See FIG. 8c). Also, by using different ratios of forward and reverse bias current the substantially constant temperature ranges A, B and C which are discussed above can be shifted in temperature by up to 10° C. This is shown in FIG. 8c in which the middle of the stable temperature region is approximately 12.5° C. as compared to FIG. 8a in which the middle of the stable temperature region is 21.5° C. Furthermore the noise for these readings was less than 0.7% of the output signal strength.

The temperature ranges discussed above over which reduced sensitivity to temperature is attained, correspond to practical operating temperatures and enable the LED arrangement according to the present invention to be stabilised with a simple thermo-electric cooler.

Figure 9:
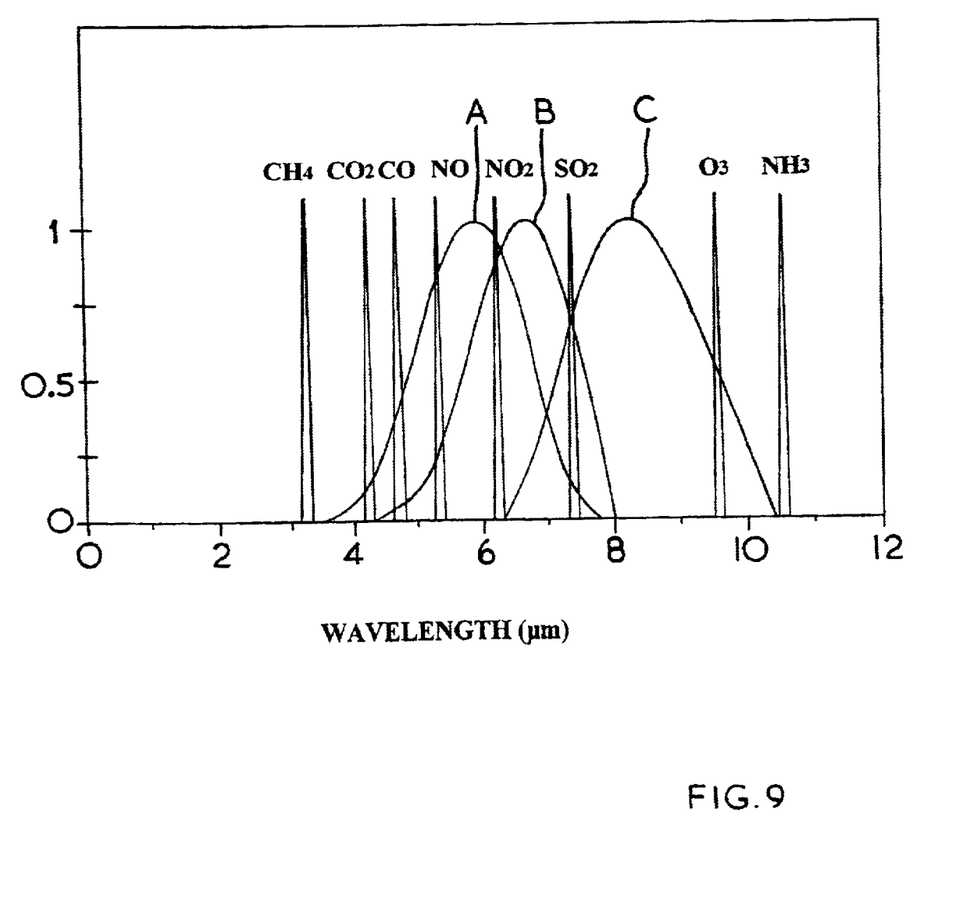
FIG. 9 shows the output emission spectra of three samples of the type of LED shown in FIG. 1.

The output emission spectra of three samples of the type of LED (30) shown in FIG. 1, are shown in FIG. 9. Spectrum A is that of an InSb infrared diode of the type described above in relation to FIGS. 1 and 3 and spectra B and C are those of two different HgCdTe infrared diodes. As a source it can be seen that the InSb diode would be useful in the detection of NO and $NO_2$ gases because vibrational-rotational absorption spikes characteristic of NO and $NO_2$ gasses lie within the spectrum A. Similarly, the HgCdTe diode with spectrum B would be useful in the detection of $NO_2$ and $SO_2$ gasses and the HgCdTe diode with spectrum C would be useful in the detection of $SO_2$ and $O_3$ gasses.

It should be noted that the difference in output power between positive and negative luminescence for different wavelengths in the spectra of these infrared diodes do not vary independently with temperature and so when the total difference in output power of the LED (30) remains substantially constant over a range of temperatures, so will the difference in output power at any wavelength.

Figure 7:
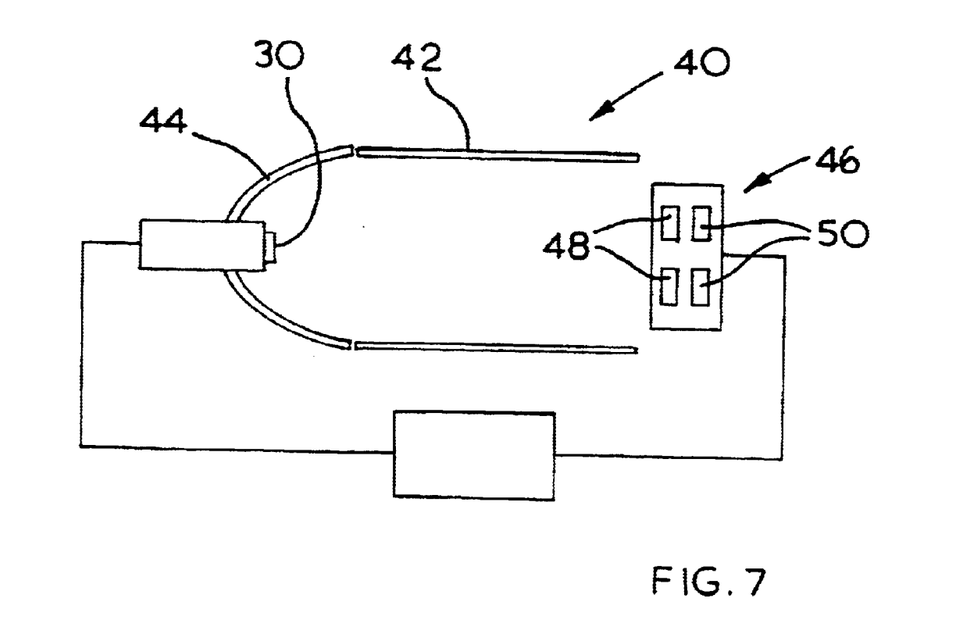
FIG. 7 schematically shows a gas detector which uses the LED of FIG. 1.

FIG. 7 shows schematically a simple design of infrared gas sensor (40) in which the LED arrangement according to the present invention can be used. The sensor (40) comprises a LED (30) as described above and driven as described above and with spectrum A of FIG. 9. The light emitted from the LED (30) is directed into a cylindrical light pipe (42) by a parabolic reflector (44). An amount of gas, for example $NO_2$ gas, to be analysed is introduced into the pipe (42). The LED (30) emits radiation at frequencies which correspond to the difference between vibration-rotational energy levels of the molecules of the $NO_2$ gas to be detected (See FIG. 9). If the gas in the pipe (42) contains some $NO_2$ some of the light emitted from the LED (30) at a characteristic wavelength of approximately 6.2 microns will be absorbed by the gas. This is because photons of light emitted by the diode will excite $NO_2$ gas molecules to a higher vibration-rotational energy level. Thus, a detector arrangement (46) located at the opposite end of the pipe (42) to the LED (30) will detect a signal of reduced power at the characteristic wavelength of 6.2 microns associated with the $NO_2$ gas.

The detector arrangement (46) may comprise one or more filters (48) which are located in front of respective detectors (50). The combination of the output spectrum of the LED (30) and the range of frequencies passed by a particular filter (48) can be used to ensure that the light reaching a particular detector (50) is associated with a characteristic absorption wavelength of a particular gas so that the strength of the signal detected by a particular detector (50) can determine whether and in what amounts the associated gas is present in the pipe (42).

What is claimed is:

1. An infrared light emitting diode (LED) arrangement comprising:
    an infrared LED (30) which emits positive luminescence when forward bias and emits negative luminescence when reverse biased;
    a drive means for supplying an alternating forward and reverse bias input to the LED;
    characterised in that the levels of forward ($+v_1$) and reverse bias ($-v_2$) applied by the drive means are set so that at the forward bias input level the change in output power of the LED with temperature is substantially equal to and cancels out the change in the output power of the LED with temperature at the reverse bias input level, over a selected temperature range so that the difference in output power between the positive luminescence and the negative luminescence of the light emitting diode is stabilised with respect to temperature.

2. An arrangement according to claim 1 wherein the alternating forward and reverse bias input alternates regularity.

3. An arrangement according to claim 1 wherein the period and intensity of the forward bias input is substantially the same in consecutive cycles of positive luminescence and the period and intensity of the reverse bias input is substantially the same in consecutive cycles of negative luminescence.

4. An arrangement according to claim 1 wherein the reverse bias input applied to the LED (30) is such that it generates the maximum level of negative luminescence in the LED, at the maximum temperature of a selected temperature range of operation.

5. An arrangement according to claim 1 wherein the light emitting diode (30) emits radiation at infrared wavelengths in the range of 3 to 13 microns.

6. An arrangement according to claim 1 wherein the light emitting diode (30) is formed from a narrow bandgap semiconductor material.

7. A sensor (40) including an infrared light emitting diode arrangement according to claim 1.

8. A sensor according to claim 7 wherein the sensor is a gas sensor.

9. A method operating an infrared light emitting diode (LED) (30) which emits positive luminescence when forward biased and emits negative luminescence when reverse biased, comprising supplying an alternating forward ($+v_1$) and reverse ($-v_2$) bias input to the light emitting diode characterised in that the levels of forward and reverse bias are selected so that the change in the output power of the LED with temperature at the forward bias input level is substantially equal to and cancels out the change in the output power of the LED with temperature at the reverse bias input level, over a selected temperature range so that the difference in output power between positive luminescence and negative luminescence of the light emitting diode is stabilised with respect to temperature.

10. A method according to claim 9 wherein the alternating forward and reverse bias input alternates regularty.

11. A method according to claim 9 wherein the period and intensity of the forward bias input is substantially the same in consecutive cycles of positive luminescence and the period and intensity of the reverse bias input is substantially the same in consecutive cycles of negative luminescence.

12. A method according to claim 9 wherein the reverse bias input applied to the LED (30) is such that it generates the maximum level of negative luminescence in the LED, at the maximum temperature in a selected temperature range of operation.

13. A method according to claim 9 wherein the light emitting diode (30) emits radiation at infrared wavelengths in the range of 3 to 13 microns.

14. A method according to claim 9 wherein the minimum level of negative luminescence of the LED is used as a base level for measurements of the output power of the LED.

15. A method of operating a sensor (40) comprising an infrared light emitting diode (LED) (30) by operating the LED according to the method of claim 9.

16. A method according to claim 15 wherein the sensor is a gas sensor.

* * * * *

UNITED STATES PATENT AND TRADEMARK OFFICE
CERTIFICATE OF CORRECTION

PATENT NO. : 6,850,013 B1
DATED : February 1, 2005
INVENTOR(S) : Ashley et al.

It is certified that error appears in the above-identified patent and that said Letters Patent is hereby corrected as shown below:

Column 4,
Line 9, "fight" should read -- light --

Column 6,
Line 48, "to the achieve" should read -- to achieve --

Column 8,
Lines 60-61, "regularity" should read -- regularly --

Column 9,
Line 16, -- of -- should be inserted after "method"

Column 10,
Line 4, "regularty" should read -- regularly --.

Signed and Sealed this

Thirty-first Day of May, 2005

JON W. DUDAS
*Director of the United States Patent and Trademark Office*